United States Patent
Matthews

(10) Patent No.: US 8,545,573 B2
(45) Date of Patent: Oct. 1, 2013

(54) SPIRAL OCCLUDING DEVICE WITH AN OCCLUSION SAIL

(75) Inventor: James Matthews, Grosse Pointe, MI (US)

(73) Assignee: Cook Medical Technologies LLC, Bloomington, IN (US)

( * ) Notice: Subject to any disclaimer, the term of this patent is extended or adjusted under 35 U.S.C. 154(b) by 822 days.

(21) Appl. No.: 12/029,828

(22) Filed: Feb. 12, 2008

(65) Prior Publication Data

US 2009/0204145 A1 Aug. 13, 2009

(51) Int. Cl.
*A61F 2/02* (2006.01)

(52) U.S. Cl.
USPC ........................................ 623/23.72

(58) Field of Classification Search
USPC ................... 606/200, 213; 623/23.72
See application file for complete search history.

(56) References Cited

U.S. PATENT DOCUMENTS

| | | | |
|---|---|---|---|
| 5,226,911 A * | 7/1993 | Chee et al. ............... | 606/191 |
| 5,658,308 A * | 8/1997 | Snyder .................... | 606/191 |
| 5,792,154 A * | 8/1998 | Doan et al. .............. | 606/151 |
| 5,843,118 A * | 12/1998 | Sepetka et al. ........... | 623/1.15 |
| 5,861,003 A | 1/1999 | Latson et al. | |
| 5,957,940 A | 9/1999 | Tanner et al. | |
| 5,976,174 A | 11/1999 | Ruiz | |
| 6,375,671 B1 | 4/2002 | Kobayashi et al. | |
| 6,623,508 B2 | 9/2003 | Shaw et al. | |
| 6,837,893 B2 | 1/2005 | Miller | |
| 2002/0026216 A1 | 2/2002 | Grimes | |
| 2003/0139819 A1 | 7/2003 | Beer et al. | |
| 2004/0044364 A1 | 3/2004 | DeVries et al. | |
| 2005/0004598 A1 * | 1/2005 | White et al. ............... | 606/200 |
| 2005/0055050 A1 | 3/2005 | Alfaro | |
| 2005/0075665 A1 | 4/2005 | Brenzel et al. | |
| 2005/0113868 A1 | 5/2005 | Devellian et al. | |
| 2005/0192654 A1 | 9/2005 | Chanduszko et al. | |
| 2005/0251201 A1 | 11/2005 | Roue et al. | |
| 2006/0052821 A1 | 3/2006 | Abbott et al. | |

* cited by examiner

*Primary Examiner* — Melanie Tyson
*Assistant Examiner* — Son Dang
(74) *Attorney, Agent, or Firm* — Brinks Hofer Gilson & Lione

(57) ABSTRACT

An occluding device designed for occlusion of fluid flow through a body cavity is disclosed. The device comprises a coil having a proximal portion and a distal portion extending longitudinally from the proximal portion. The coil has an initial tension along the distal and proximal portions and is configured have a general helical shape in an expanded state. The device further comprises a first set of fibers attached to the coil and extending therefrom for occlusion of the body cavity. The device further comprises a second set of fibers attached to the coil at a plurality of areas longitudinally along the coil, defining an occlusion sail disposed longitudinally along the coil at the plurality of areas therealong. The second set of fibers is configured have the general helical shape when the coil is in the expanded state for enhanced occlusion of the body cavity.

11 Claims, 5 Drawing Sheets

SPIRAL OCCLUDING DEVICE WITH AN OCCLUSION SAIL

BACKGROUND OF THE INVENTION

The present invention relates to medical devices. More particularly, the invention relates to occluding devices having occlusion sails and methods of occluding fluid flow through a body vessel.

Pushable fibered coils have been used as a primary occluding device for treatment of various arteriovenous malformations (AVM) and varicoceles, as well as for many other arteriovenous abnormalities in the body. Occluding devices are also used to repair abnormal shunts between arteries and veins, prevent or reduce blood flow to tumors, stop hemorrhaging as a result of trauma, and stabilize aneurysms to prevent rupture. Pushable fibered coils may be configured in a variety of sizes with varying diameters and may be made of several different materials including stainless steel and platinum. Occlusion devices may vary for differing purposes, e.g., to hold the device in place within a cavity or vessel and to pack the device within the vessel for enhanced occlusion.

Although current pushable fibered coils are adequate, such coils may be improved for more effective occlusion of fluid flow through a lumen of a body vessel without compromising the cross-sectional profile of each of the coils. Many medical procedures for occluding blood flow through an artery or vein require a number of coils having a relatively large cross-sectional profile. Moreover, one coil or two may not be sufficient to effectively occlude blood flow through a lumen of an artery or vein. In many current procedures, many coils may be packed within each other to produce effective cross sectional occlusion of fluid flow through a body vessel. In some instances, these procedures may involve an undesirable amount of additional time and costs.

BRIEF SUMMARY OF THE INVENTION

The present invention generally provides an occluding device that provides an enhanced surface area occlusion while minimizing cross-sectional profile of the device during deployment. In one embodiment, the present invention provides an occluding device for occlusion of a body cavity or vessel. The device comprises a coil having a proximal portion and a distal portion extending longitudinally from the proximal portion. The coil has an initial tension along the distal and proximal portions and is configured have a general helical shape in an expanded state. The device further comprises a first set of fibers attached to the coil and extending therefrom for occlusion of the body cavity. The device further comprises a second set of fibers attached to the coil at a plurality of areas longitudinally along the coil, defining an occlusion sail disposed longitudinally along the coil at the plurality of areas therealong. The second set of fibers is configured take on the general helical shape when the coil is in the expanded state for enhanced occlusion of the body cavity.

In another embodiment, the present invention provides an embolization kit for occluding fluid flow through a body vessel. The kit comprises a guide catheter and an inner catheter having proximal and distal ends and being configured to be passed through the guide catheter to position the inner catheter in the body vessel. The inner catheter has hub adjacent the proximal end. The kit further comprises the occluding device mentioned above.

In another example, the present invention provides a method of occluding fluid flow through a body vessel. The method comprises providing an occluding device comprising a coil and fibers attached to the coil at a plurality of areas longitudinally along the coil to define an occlusion sail disposed longitudinally along the coil for enhanced occlusion of the body cavity. The method further comprises deploying the distal portion at a desired point of occlusion in the body vessel to hold the device in place within the body vessel. The method further comprises deploying the proximal portion across the lumen of the body vessel within the distal portion to pack the coil and occlude the body vessel.

Further objects, features, and advantages of the present invention will become apparent from consideration of the following description and the appended claims when taken in connection with the accompanying drawings.

DETAILED DESCRIPTION OF THE INVENTION

The present invention generally provides an occluding device having enhanced occluding features without affecting the cross-sectional profile of the device. The device comprises a coil and used for transcatheter embolization. The coil has a set of fibers attached thereto at a plurality of areas longitudinally along the coil, defining an occlusion sail. The occlusion sail provides increased surface area contact for enhanced occlusion in a body vessel without compromising with a relatively large cross-sectional profile.

The occluding device may be used to occlude fluid flow through a body vessel due to a blood vessel malformation occurring in the brain, like aneurysms, or another part of the body. The occluding device also may be used for treatment of renal arteriovenous malfunction (AVM), pulmonary AVM, vascular tumors, low-flow fistulas, trauma related hemorrhages, and visceral vasculature defects including varicoceles, and aneurysms. For example, treatment of visceral vasculature defects may include but are not limited to embolotherapy on gastroduogenal hemorrhages, hepatic aneurysms, celiac aneurysms, internal iliac aneurysms, and internal spermatic varicoceles.

Figure 1:
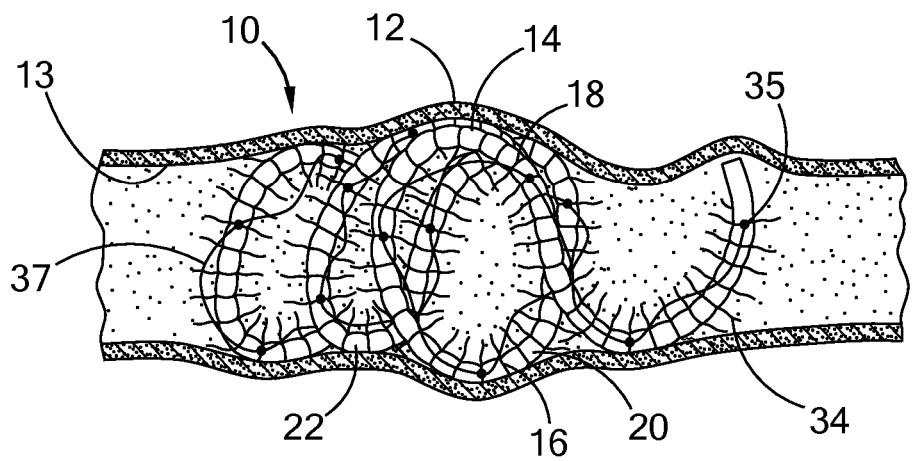
FIG. 1 is an environmental side view of an occluding device with an occlusion sail deployed in a body vessel in accordance with one embodiment of the present invention.

FIG. 1 illustrates an occluding device 10 in a deployed state for occlusion of fluid flow through a lumen of a body vessel 12 in accordance with one embodiment of the present invention. As shown in FIG. 1, the occluding device 10 is positioned to engage an inner wall 13 of the body vessel 12 and comprises a primary coil 14 and a secondary coil 16. Preferably, the primary coil 14 comprises a primary body 18 that has a helical shape and forms the secondary coil 16. The secondary coil 16 comprises a secondary body 20 that forms a series of loops 22. The series of loops 22 define a cross-sectional area formed axially along the secondary coil 16.

Figure 2A:
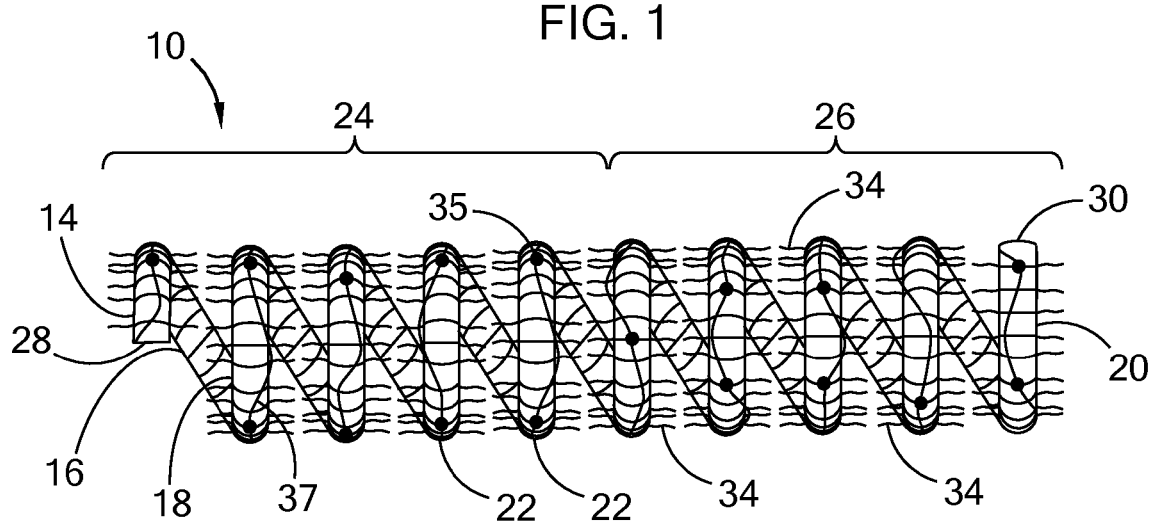
FIG. 2a is a side view of an occluding device with an occluding sail in accordance with one embodiment of the present invention.
Figure 2B:
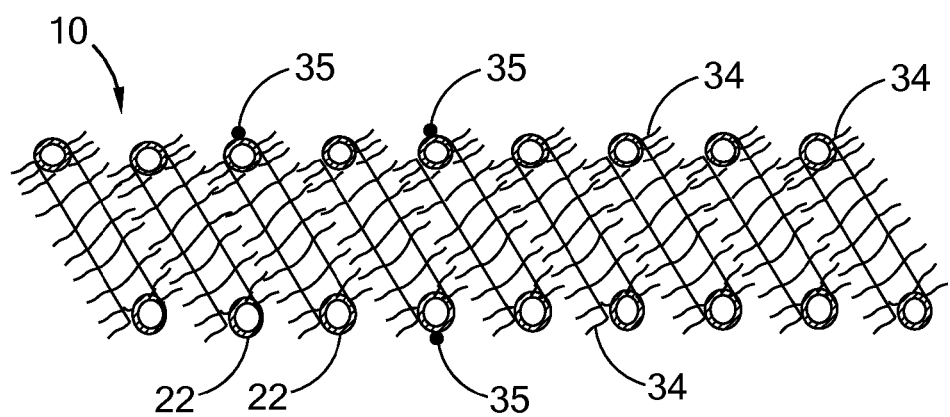
FIG. 2b is a cross-sectional view of the occluding device in FIG. 2a taken along line 2-2.

As shown in FIGS. 1-2b, the primary coil 14 further comprises a proximal portion 24 and a distal portion 26 integrally extending longitudinally from the proximal portion 24. In this embodiment, the proximal portion 24 extends from a proximal end 28 to the distal portion 26 extending to a distal end 30 of the occluding device 10. In a deployed or an expanded state, the primary coil takes on a generally helical shape. Preferably, to assist in occluding fluid flow through the lumen of the body vessel 12, the proximal portion 24 and the distal portion 26 of the primary coil 14 further include a first set of fibers 34 attached between loops of the primary coil 14 and extending therefrom.

As shown, the primary coil 14 further includes a second set of fibers 35 attached thereto preferably at a plurality of locations longitudinally along the coil 14 to define an occlusion sail 37 disposed longitudinally along the coil. In this example, the second set of fibers 35 is configured to have the generally helical shape when the coil 14 is in the expanded state for enhanced occlusion of the body vessel. The second set of fibers 35 provide enhanced occlusion by increasing surface area contact within a body vessel without compromising significant cross-sectional profile of the device in the undeployed or collapsed state.

In this embodiment of the present invention, the primary coil 14 has an initial tension along the proximal and distal portions thereof. Preferably, the initial tension of the primary coil 14 is between about 5 and 120 grams of weight, and preferably between about 30 and 100 grams of weight. Initial tension may be defined to be the amount of force required to cause a 4 centimeter length of coil to begin to elongate. The initial tension may also be defined by the amount of force required to cause a coil to begin elongating at a ratio of between about 1.25 to 15 grams per centimeter, and preferably between about 2.5 to 7.5 grams per centimeter.

As shown in FIGS. 2a and 2b, the occluding device 10 comprises the primary coil 14 formed to define the secondary coil 16. The primary coil 14 has a generally helical shape that forms the primary body 18 and comprises of the proximal and distal portions. The secondary coil 16 comprises the secondary body 20 and forms the series of loops 22. Preferably, the secondary body 20 has a length of between about 2 to 30 centimeters. As shown in FIG. 2a, the series of loops 22 define a cross-sectional lumen formed axially along the length of the secondary coil 16 and is preferably spaced apart by up to about 5 millimeters of curl space.

Preferably, the occluding device 10 further includes the first and second sets of fibers 34, 36 wedged or attached to the primary coil 14 and extending therefrom. As mentioned above, the second set of fibers 35 are attached at various locations longitudinally along the primary coil 14. In this embodiment, as shown in FIG. 2a, the series of loops 22 along the secondary coil 16 has a curl space and outside diameter between each loop. When in the expanded state, the second set of fibers 35 take on a helical shape consistent with the series of loops 22, since the fibers are attached at a plurality of locations longitudinally along the primary coil 14.

Figure 3A:
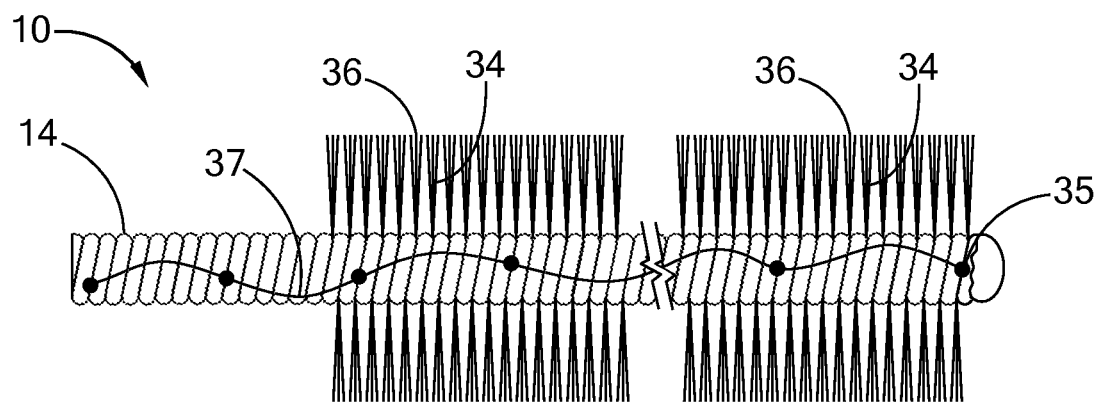
FIG. 3a is a side view of a primary coil of the device in FIG. 1 in accordance with one embodiment of the present invention.
Figure 3B:
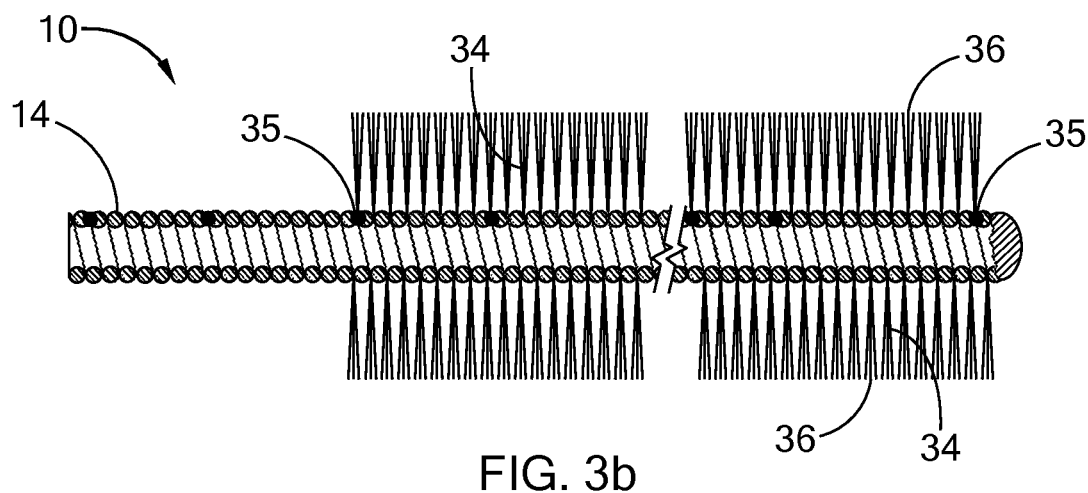
FIG. 3b is a cross-sectional view of the primary coil in FIG. 3a taken along line 3-3.

As shown in FIGS. 3a and 3b, the fibers 34 are spaced apart from each other and are held between helical loops of the primary coil 14. Preferably, the first set of fibers 34 include strands 36 and the second set of fibers 35 include strands 37, both of which are comprised of a synthetic polymer such as a polyester textile fiber, e.g., DACRON™. Preferably, the strands 37 are held between loops longitudinally along the primary coil. As desired, the strands 36 may be held between adjacent loops, alternating loops, alternating double loops, or any desired configuration.

Preferably, the strands 36 have a length extending from the primary coil 14 of between 3 to 8 millimeters, and preferably between about 5 to 6 millimeters as desired. In this embodiment, the fibers are spaced apart from each other by about 1 to 2 millimeters. In this embodiment, the strands 37 have a length that may vary between about 3 and 20 centimeters. Preferably, the strands 36 and 37 have an outer diameter of about 0.00050 to 0.00100 inch.

Figure 4:
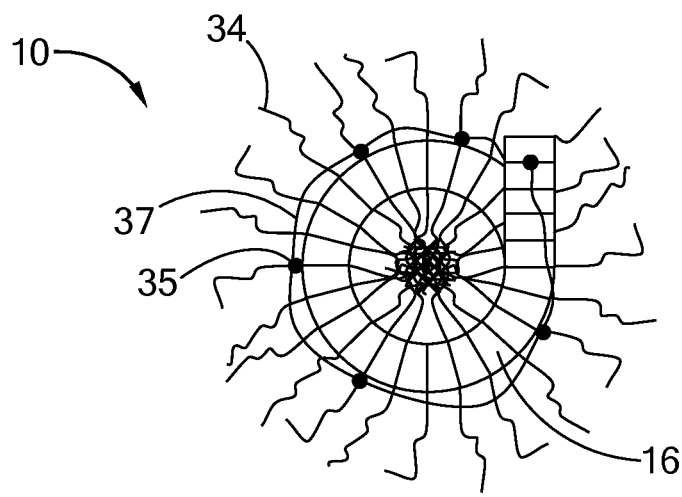
FIG. 4 is an end view of the occluding device.

FIG. 4 illustrates an end view of the occluding device 10. The secondary coil 16 may have an outside diameter ranging from about 3 to 15 millimeters. In accordance with one embodiment, the distal portion 26 of the occluding device 10 may have a less, the same, or a greater outside diameter than the proximal portion 24. The proximal portion 24 may have a variable outside diameter along the length of the secondary coil 16, creating the series of loops 22 with variable diameter.

As shown, the second set of fibers take on a generally helical shape consistent with generally helical shape of the primary coil 14. However, as shown, the second set of fibers further fill the cross-sectional area of the coil 14 as each fiber is not completely attached to the coil 14, but merely attached at a number of longitudinal locations along the coil 14. This allows for the fibers to be loosely attached thereto to follow a helical shape yet be able to further occupy an increased surface area or cross-sectional area of the body vessel for enhanced occlusion thereof. Additionally, the longitudinally placement of the fibers along the coil 14 provides a device having enhanced occluding features without compromising cross-sectional profile in the collapsed state.

In one embodiment, the occluding device 10 may comprise of at least one or more metals and metal alloys to create variable rigidity along the length of the primary coil 14. In this embodiment, the primary coil 14 may comprise platinum and platinum alloys. In another embodiment, the distal portion may be comprised generally of palladium and the proximal portion may comprise a less rigid alloy, e.g., palladium alloy.

In another embodiment, the distal portion 26 of the primary coil 14 may have a tensile strength of between about 50,000 and 400,000 pounds per square inch. It has been determined that the tensile strength range described above provides the proximal portion with the capability of being flexible, malleable, and folded.

At least part of the device 10 may be made of any suitable material including, in one embodiment, a superelastic material, stainless steel wire, cobalt-chromium-nickel-molybdenum-iron alloy, or cobalt-chrome alloy. It is understood that the device 10 may also be formed of any suitable material that will result in a self-opening or self-expanding device 10, such as shape memory materials. Shape memory materials or alloys have the desirable property of becoming rigid, i.e., returning to a remembered state, when heated above a transition temperature. A shape memory alloy suitable for the present invention is Ni—Ti available under the more commonly known name Nitinol. When this material is heated above the transition temperature, the material undergoes a phase transformation from martensite to austenic, such that the material returns to its remembered state. The transition temperature is dependent on the relative proportions of the alloying elements Ni and Ti and the optional inclusion of alloying additives.

In one example, the device 10 may be made of Nitinol with a transition temperature that is slightly below normal body temperature of humans, which is about 98.6° F. Thus, when the device 10 is deployed in a body vessel and exposed to normal body temperature, the alloy of the device 10 will transform to austenite, that is, the remembered state, which for one embodiment of the present invention is the expanded state when the device 10 is deployed in the body vessel. To remove the device 10 it is cooled to transform the material to martensite which is more ductile than austenite, making the device 10 more malleable. As such, the device 10 can be more easily collapsed and pulled into a lumen of a catheter for removal.

In another example, the device 10 may be made of Nitinol with a transition temperature that is above normal body temperature of humans, which is about 98.6° F. Thus, when the device 10 is deployed in a body vessel and exposed to normal body temperature, the device 10 is in the martensitic state so that the device 10 is sufficiently ductile to bend or form into a desired shape. To remove the device 10, the device 10 is heated to transform the alloy to austenite so that it becomes rigid and returns to a remembered state.

Figure 5A:
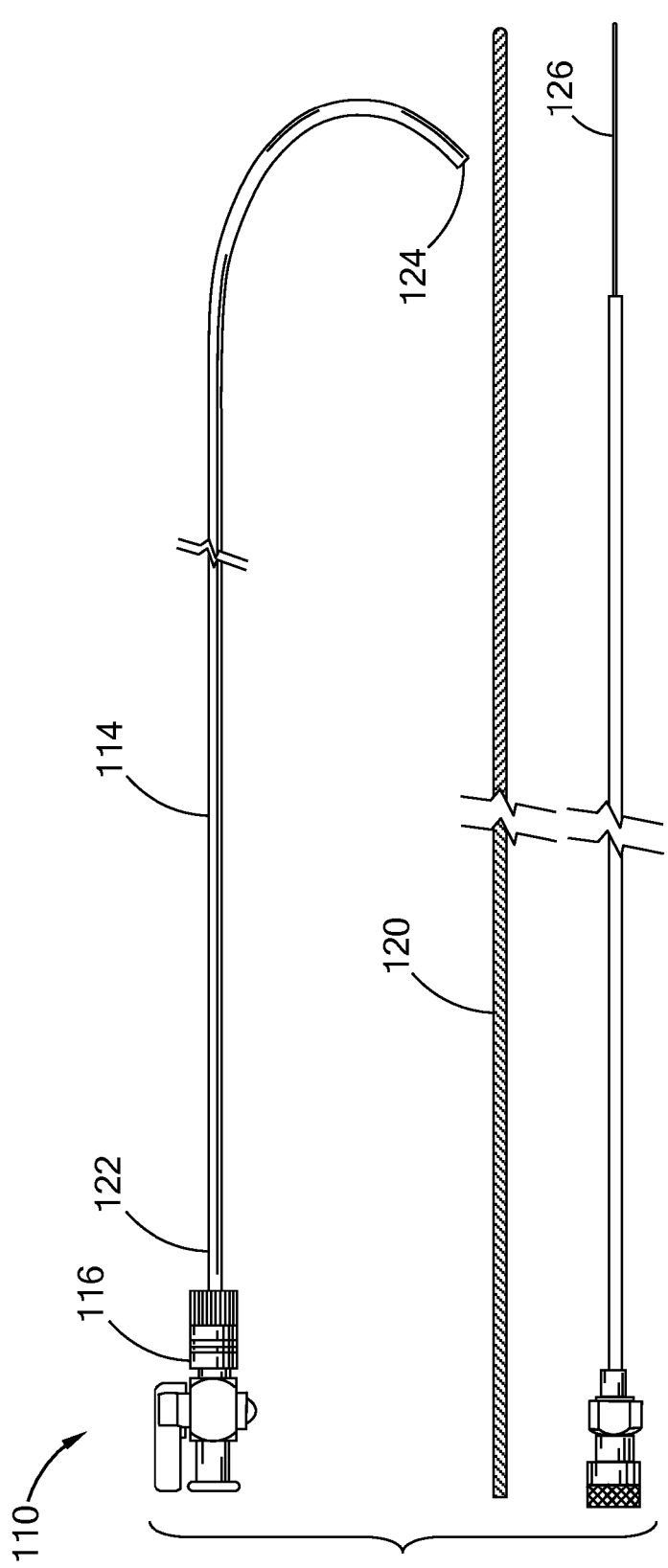
FIG. 5a is an exploded view of an embolization kit for the occluding device in accordance with one embodiment of the present invention.
Figure 5B:
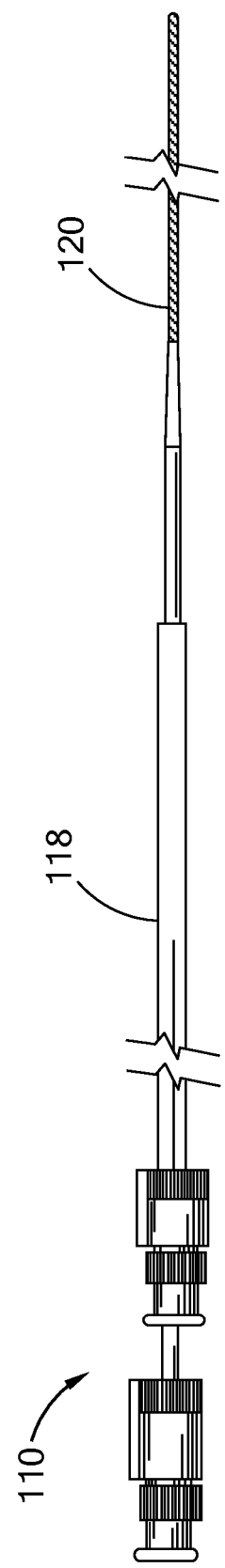
FIG. 5b is a side view of the embolization kit.

FIGS. 5a and 5b illustrate a body cavity embolization kit 110 which implements the occluding device in accordance with one embodiment of the present invention. As shown, the kit 110 includes an inner catheter 114 preferably made from a soft, flexible material such as silicone or any other suitable material. Generally, the inner catheter 114 has a proximal end 122, a distal end 124, and a plastic adapter or hub 116 to receive apparatus to be advanced therethrough. In this embodiment, the inside diameter of the inner catheter may range between 0.014 and 0.027 inch. The kit 110 further includes a guide wire 120 which provides the guide catheter 118 a path during insertion of the guide catheter 118 within a body cavity. The size of the wire guide is based on the inside diameter of the guide catheter.

In this embodiment, the kit 110 further includes a polytetrafluoroethylene (PTFE) guide catheter or sheath 118 for percutaneously introducing the inner catheter 114 in a body cavity. Of course, any other suitable material may be used without falling beyond the scope or spirit of the present invention. The guide catheter 118 may have a size of about 4-French to 8-French and allows the inner catheter 114 to be inserted therethrough to a desired location in the body cavity. The guide catheter 118 receives the inner catheter 114 and provides stability of the inner catheter 114 at a desired location of the body cavity. For example, the guide catheter 118 may stay stationary within a common visceral artery, e.g., a common hepatic artery, and add stability to the inner catheter 114 as the inner catheter is advanced through the guide catheter to a point of occlusion in a connecting artery, e.g., the left or right hepatic artery.

When the distal end 124 of the inner catheter 114 is at the point of occlusion in the body cavity, the occluding device is loaded at the proximal end 122 of the inner catheter 114 and is advanced through the inner catheter for deployment through the distal end 124. In this embodiment, a push wire 126 is used to mechanically advance or push the occluding device through the inner catheter 114. The size of the push wire used depends on the diameters of the inner catheter. As mentioned above, the distal portion 26 serves to hold the coil in place along the inner wall of the body cavity 13. The proximal portion 24 and fibers 34 serve to occlude fluid passage by filling the lumen of the body cavity 12.

It is to be understood that the body cavity embolization kit 110 described above is merely one example of a kit that may be used to deploy the occluding device in a body vessel. Of course, other kits, assemblies, and systems may be used to deploy any embodiment of the occluding device without falling beyond the scope or spirit of the present invention.

Figure 6:
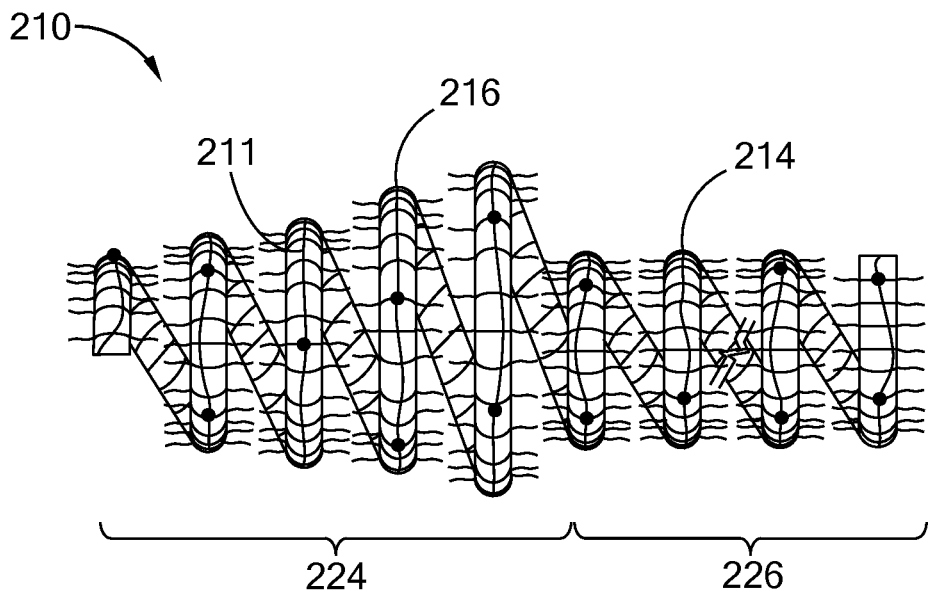
FIG. 6 is a side view of an occluding device in accordance with another embodiment of the present invention.

FIG. 6 illustrates an occluding device 210 having an occlusion sail 211 in accordance with another embodiment of the present invention. As shown, the device 210 includes a proximal portion 224 of a secondary coil 216 having a variable outside diameter. In this embodiment, the secondary coil 216 proximally tapers along the proximal portion 224 as the second set of fiber is attached at various locations longitudinally along the primary coil 214. Preferably, the proximal portion 224 has a relatively larger outside diameter than the outside diameter of the distal portion 226 of the secondary coil 216. The variable outside diameter of the proximal portion of the secondary coil 216 provides further enhanced packing of the device 210 for enhanced occlusion.

Figure 7:
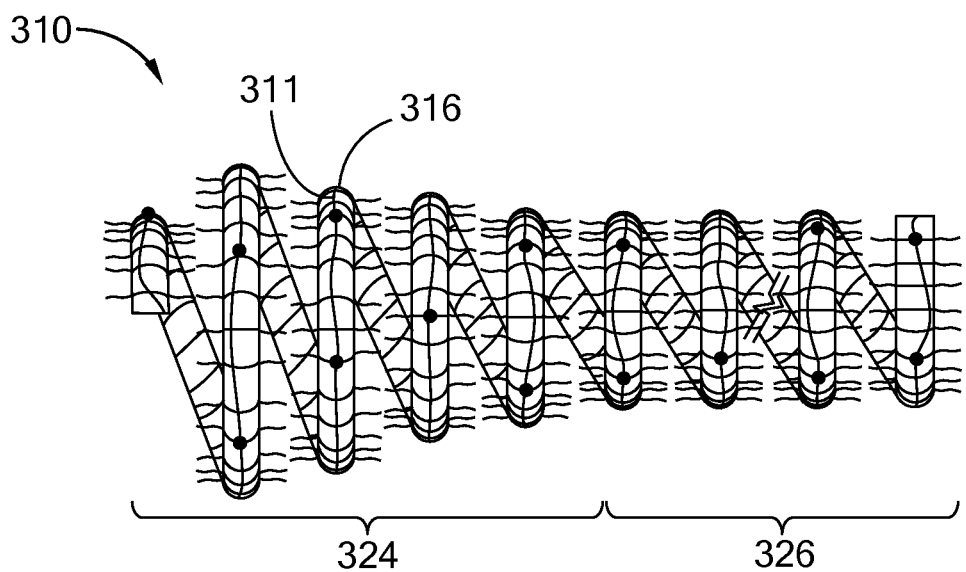
FIG. 7 is a side view of an occluding device in accordance with yet another embodiment of the present invention.

FIG. 7 illustrates another occluding device 310 having an occlusion sail 311 in accordance with yet another embodiment of the present invention. As shown, the device 310 includes a proximal portion 324 of a secondary coil 316 having a variable outside diameter. In this embodiment, the secondary coil 316 proximally flares along the proximal portion 324 as the second set of fiber is attached at various locations longitudinally along the primary coil 314. Preferably, the proximal portion 324 has a relatively larger outside diameter than the outside diameter of the distal portion 326 of the secondary coil 316. The variable outside diameter of the proximal portion of the secondary coil provides further enhanced packing of the device for enhanced occlusion.

Figure 8:
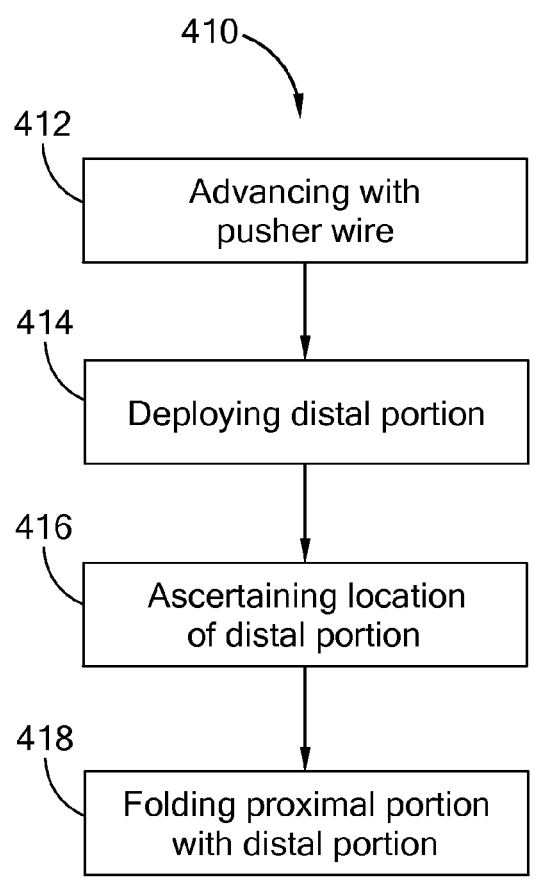
FIG. 8 is a flowchart of a push embolization method in accordance with one example of the present invention.

The occluding device may be deployed in a body vessel by a push embolization method or a squirt embolization method in accordance with the present invention. FIG. 8 depicts a push embolization method 410 of transcatheter embolization using an embodiment of the occluding device. As typically performed in embolotherapy, an introducer or a guide catheter is percutaneously introduced into the body vessel of a patient and an inner catheter is passed through the guide catheter to position the inner catheter at a desired point of occlusion in the body vessel.

The occluding device, which is elongated to its full length within a cartridge, is loaded in the hub at the proximal end of the inner catheter. In step 412, the device is advanced by the pusher wire in accordance with this method of deploying the occluding device.

In step 414, a first portion of the distal portion of the occluding device, e.g., a first loop of the secondary coil, is deployed at the desired point of occlusion in the body vessel as a remaining portion of the occluding device is held in the inner catheter. The first portion of the coil may be between about 5% to 10% of the length of the coil. The first portion begins to hold the device in place within the vessel and the remainder of the distal portion further enhances this feature. In step 416, the location of the first portion in the body vessel is ascertained by any suitable means, such as by fluoroscopy, relative to the body vessel. When the distal portion is at the desired point of occlusion in the body vessel, the proximal portion is folded across the lumen of the body vessel to pack the coil and occlude the body vessel in step 418. Preferably, the proximal portion is folded within the distal portion by moving the catheter reciprocally back and forth relative to the body vessel as the proximal portion is deployed from the inner catheter. As a length of the proximal portion is being deployed, the distal end of the inner catheter is moved back. The inner catheter is then moved forward against the length of the proximal portion, thereby folding the length of the proximal portion at the desired point of occlusion. The inner catheter is moved back and forth until the proximal portion is folded within the distal portion and the occluding device is in a packed state.

However, if it is ascertained in step 416 that the distal portion of the occluding device is not at the desired point of occlusion, then the position of the inner catheter is moved fore or aft relative to the body vessel such that the distal portion is placed at the desired point of occlusion.

Figure 9:
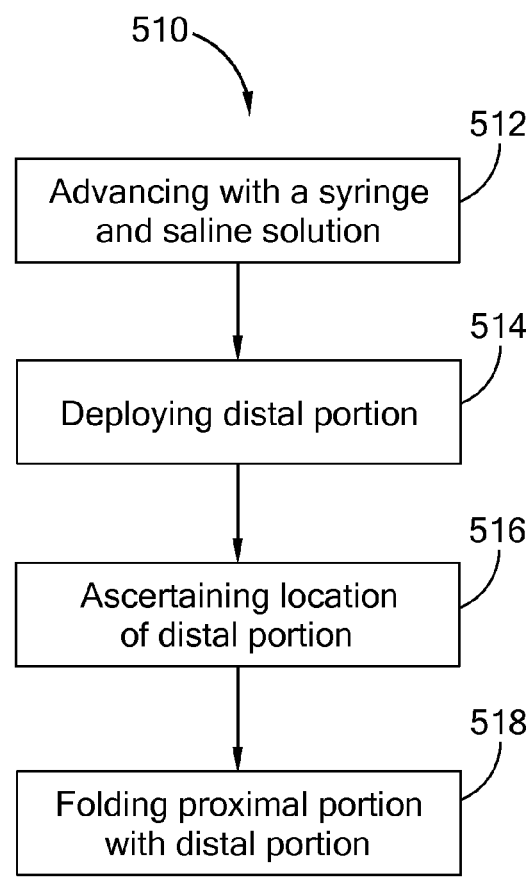
FIG. 9 is a flowchart of a squirt embolization method in accordance with one example of the present invention.

FIG. 9 illustrates a squirt embolization method 510 of transcatheter embolization using an embodiment of the occluding device of the present invention. As typically performed in embolotherapy, a guide catheter is introduced into the body vessel as described above in the push embolization method. Once the inner catheter is passed through the guide catheter and the occluding device is loaded at the hub of the inner catheter, the occluding device is advanced in step 512 through the inner catheter with use of a luer lock syringe and saline solution. In step 514, a first portion of the distal portion, e.g., a first loop of the secondary coil, is deployed at the desired point of occlusion in the body vessel as a remaining portion of the distal portion is held in the inner catheter. The first portion of the coil may be between about 5% to 10% of the length of the coil.

In step 516, the location of the first portion in the body vessel is ascertained by any suitable means, such as by fluoroscopy, relative to the body vessel. If the first portion of the coil is at the desired point of occlusion in the body vessel, then the remaining portion is introduced together with the first portion with the saline solution. The distal portion holds the device in place within the vessel. Then, the proximal portion is packed within the distal portion to occlude the body vessel. Preferably, the proximal portion is folded by moving the distal end of the inner catheter reciprocally back and forth relative to the body vessel as described above to pack the coil and occlude the body vessel. However, if it is ascertained in step 516 that the first portion is not at the desired point of occlusion, then the position of the inner catheter is moved fore or aft relative to the body vessel such that the first loop is placed at the desired point of occlusion.

While the present invention has been described in terms of preferred embodiments, it will be understood, of course, that the invention is not limited thereto since modifications may be made to those skilled in the art, particularly in light of the foregoing teachings.

The invention claimed is:

1. An occluding device for occlusion of a body cavity, the device comprising:
a primary coil having a proximal end, a proximal portion, a distal portion, and a distal end, the proximal portion extending longitudinally from the proximal end to the distal portion, the distal portion extending longitudinally from the proximal portion to the distal end, the primary coil having an initial tension along the distal and proximal portions and being configured to form a secondary coil having a general helical shape in an expanded state;
a set of first fibers attached to the primary coil and extending therefrom for occlusion of the body cavity along at least the distal portion of the primary coil; and
a set of second fibers attached to the primary coil at a plurality of areas longitudinally along the primary coil at radially outer locations of the secondary coil, the set of second fibers comprising a plurality of strands, each strand of the set of second fibers being at least twice as long as each of the first fibers and attached to the primary coil at a plurality of longitudinal locations along the primary coil and extending longitudinally along the primary coil substantially from the proximal end of the coil to the distal end of the coil, the set of second fibers defining an occlusion sail disposed longitudinally along the primary coil, the set of second fibers being configured to follow the general helical shape of the secondary coil when the coil is in the expanded state for enhanced occlusion of the body cavity.

2. The device of claim 1 wherein the secondary coil has a series of loops axially spaced apart by up to about 5 millimeters curl space.

3. The device of claim 2 wherein the secondary coil has a variable outside diameter, the variable outside diameter being configured to proximally flare along the length of the proximal portion.

4. The device of claim 1 wherein the initial tension is between about 5 and 120 grams of weight.

5. The device of claim 2 wherein the secondary coil has a variable outside diameter configured to proximally taper along the length of the proximal portion.

6. The device of claim 1 wherein the primary coil has a tensile strength of between about 50,000 and 400,000 pounds per square inch.

7. The device of claim 1 wherein the primary coil has a length of between about 3 and 20 centimeters and wherein the occlusion sail has a length of between about 3 and 20 centimeters.

8. The device of claim 1 wherein the fibers are made of a synthetic polyester textile fiber.

9. The device of claim 1 wherein the secondary coil has a series of loops, the set of first fibers and the set of second fibers including strands attached to the series of loops.

10. The device of claim 9 wherein each of the strands of the set of second fibers has a length of between about 3 to 20 centimeters and has an outer diameter of about 0.00050 to 0.00100 inch.

11. The device of claim 1, wherein the set of second fibers is loosely attached to the coil, such that the set of second fibers increases a cross-sectional profile of the device in the expanded state by a greater amount than in a collapsed state.

* * * * *